US 8,340,243 B2

(12) United States Patent
Ouchi et al.

(10) Patent No.: US 8,340,243 B2
(45) Date of Patent: *Dec. 25, 2012

(54) X-RAY IMAGING APPARATUS, X-RAY IMAGING METHOD, AND X-RAY IMAGING PROGRAM

(75) Inventors: Chidane Ouchi, Utsunomiya (JP); Kentaro Nagai, Yokohama (JP); Toru Den, Tokyo (JP); Hidenosuke Itoh, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/190,770

(22) Filed: Jul. 26, 2011

(65) Prior Publication Data

US 2011/0280368 A1 Nov. 17, 2011

Related U.S. Application Data

(63) Continuation of application No. 12/842,937, filed on Jul. 23, 2010, now Pat. No. 8,009,797, which is a continuation of application No. PCT/JP2009/068434, filed on Oct. 27, 2009.

(30) Foreign Application Priority Data

Oct. 29, 2008 (JP) ................................. 2008-278425

(51) Int. Cl.
*G03H 5/00* (2006.01)
(52) U.S. Cl. ........................................... 378/36; 378/62
(58) Field of Classification Search ................... 378/36, 378/62, 82

See application file for complete search history.

(56) References Cited

U.S. PATENT DOCUMENTS

| 8,009,797 B2 * | 8/2011 | Ouchi et al. ............... 378/36 |
| 2005/0117699 A1 | 6/2005 | Yoneyama |
| 2005/0286680 A1 | 12/2005 | Momose |

FOREIGN PATENT DOCUMENTS

| CN | 1523448 A | 8/2004 |
| CN | 101013613 A | 8/2007 |
| DE | 102006037257 A1 | 8/2007 |

OTHER PUBLICATIONS

Jiang et al., "X-ray Phase-Contrast Imaging with Three 2D Gratings" International Journal of Biomedical Imaging, 2007, pp. 1-8, vol. 2008, Hindawi Publishing Corporation.

Chen Bo, "Related Optical Problem Research on X-Ray phase contrast imaging," China Doctoral Dissertations Full-text Database, fundamental science edition issue 3, published Sep. 15, 2007; 120 pages (English Abstract pp. 4-5).

* cited by examiner

*Primary Examiner* — Courtney Thomas
(74) *Attorney, Agent, or Firm* — Canon U.S.A., Inc. IP Division

(57) ABSTRACT

An X-ray imaging apparatus includes a phase grating, an absorption grating, a detector, and an arithmetic unit. The arithmetic unit executes a Fourier transform step of performing Fourier transform for an intensity distribution of a Moiré acquired by the detector, and acquiring a spatial frequency spectrum. Also, the arithmetic unit executes a phase retrieval step of separating a spectrum corresponding to a carrier frequency from a spatial frequency spectrum acquired in the Fourier transform step, performing inverse Fourier transform for the separated spectrum, and acquiring a differential phase image.

13 Claims, 9 Drawing Sheets

X-RAY IMAGING APPARATUS, X-RAY IMAGING METHOD, AND X-RAY IMAGING PROGRAM

This application is a Continuation of prior U.S. patent application Ser. No. 12/842,937 filed Jul. 23, 2010, which is a Continuation of International Application No. PCT/JP2009/068434, filed Oct. 27, 2009, which claims the benefit of Japanese Patent Application No. 2008-278425, filed Oct. 29, 2008. The disclosures of the above-named applications are hereby incorporated by reference herein in their entirety.

TECHNICAL FIELD

The present invention relates to an X-ray imaging apparatus, an X-ray imaging method, and an X-ray imaging program.

BACKGROUND ART

Since X-rays have high substance transmittivity and can perform imaging with high spatial resolution, for example, X-rays are used for nondestructive inspection of subjects in industrial use, and for radiography in medical use. In these cases, a contrast image is formed by using a difference of X-ray absorption coefficient for substances, or living bodies when x-ray transmits through the substances or living bodies, depending on constituent elements or due to a difference in densities of the substances or living bodies. Such an imaging method is called X-ray absorption contrast method. However, a light element absorbs X-ray by a very small amount. It is difficult to image living soft tissues made of carbon, hydrogen, oxygen, etc., which are constituent elements of a living body, or soft materials by the X-ray absorption contrast method.

On the contrary to this, as a method for clearly imaging even tissues made of light elements, X-ray phase-contrast methods using a phase difference of X-rays have been studied since the nineteen-nineties.

A large number of X-ray phase-contrast methods have been developed. One of such methods may be an X-ray phase-contrast method using Talbot interference as a method capable of using a conventional X-ray tube (Patent literature 1).

The method using the Talbot interference described in Patent literature 1 includes an X-ray tube that generates X-rays, a phase grating that modulates the phase of the X-rays and generates an interference intensity distribution, an absorption grating that converts the interference intensity distribution into an intensity distribution of a Moiré, and an X-ray detector that detects the interference intensity distribution.

In the method described in Patent literature 1, imaging is performed by scanning the absorption grating along the direction of the grating period. With this scanning, the Moiré to be detected is moved. When the scanning length reaches one period of the absorption grating, the image of the Moiré is retrieved to the original state. Arithmetic processing is performed using at least three images of image data during scanning, and thus a differential phase image is acquired.

The method described in Patent literature 1 acquires a differential phase image by performing imaging for at least three images, and calculates a phase image from the differential phase image.

Since the method described in Patent literature 1 has to perform imaging for at least three images, if a subject is moved during imaging, image quality may be degraded.

Also, if the period of time for imaging increases, the X-ray dose for a subject increases. It is not desirable for medical use.

The present invention provides an X-ray imaging apparatus, an X-ray imaging method, and an X-ray imaging method that can acquire a differential phase image or a phase image of a subject by at least a single imaging operation.

CITATION LIST

Patent Literature

PTL 1: U.S. Pat. No. 7,180,979

SUMMARY OF INVENTION

An X-ray imaging apparatus according to the present invention includes an X-ray source; a phase grating that transmits X-rays from the X-ray source and forms an interference intensity distribution by the Talbot effect; an absorption grating that partly shields the interference intensity distribution formed by the phase grating and generates a Moiré; a detector that detects an intensity distribution of the Moiré generated by the absorption grating; and an arithmetic unit that images information of a subject from the intensity distribution of the Moiré detected by the detector and outputs the information. The arithmetic unit executes a process including a Fourier transform step of performing Fourier transform for the intensity distribution of the Moiré acquired by the detector and acquiring a spatial frequency spectrum, and a phase retrieval step of separating a spectrum corresponding to a carrier frequency from the spatial frequency spectrum acquired in the Fourier transform step, performing inverse Fourier transform for the separated spectrum, and acquiring a differential phase image.

Further features of the present invention will become apparent from the following description of exemplary embodiments with reference to the attached drawings.

DESCRIPTION OF EMBODIMENTS

First Embodiment

Figure 1:
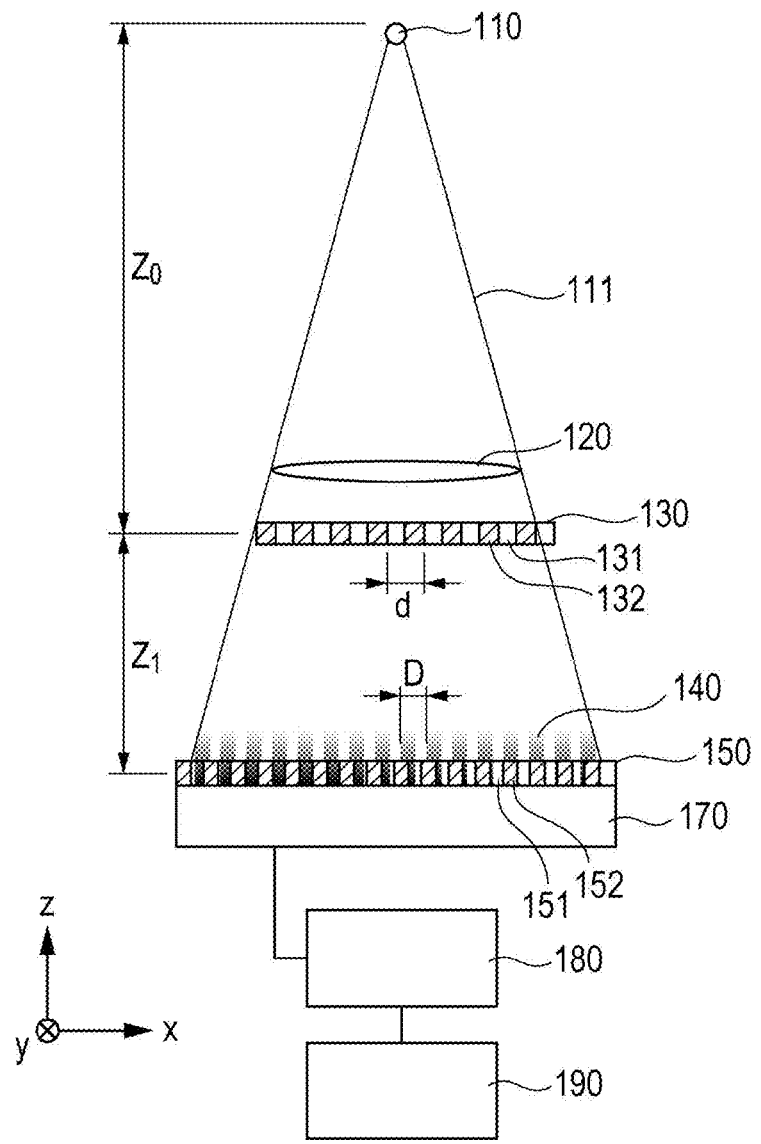
FIG. 1 is an explanatory view of an X-ray imaging apparatus according to a first embodiment of the present invention.

FIG. 1 illustrates an exemplary configuration of an X-ray imaging apparatus using Talbot interference. A process to acquire a phase image by using the X-ray imaging apparatus will be described in detail.
(X-Ray Source)
X-rays 111 generated by an X-ray source 110 are transmitted through a subject 120. When the X-rays 111 are transmitted through the subject 120, the phase of the X-rays 111 is changed and the X-rays 111 is absorbed depending on the composition, shape, etc., of the subject 120.

The X-rays may be continuous X-rays or characteristic X-rays. The wavelength of the X-rays is selected in a range from about 0.1 Å to 5 Å. A wavelength selection filter and/or a grating for a source may be provided downstream of the X-ray source 110.
(Phase Grating)
The X-rays 111 transmitted through the subject 120 is transmitted through a phase grating 130. Then, the x-rays 111 form an interference intensity distribution 140 by the Talbot effect.

The phase grating 130 is arranged upstream or downstream of the subject 120.

The phase grating 130 includes phase advance portions 131 and phase lag portions 132, which are formed by periodically changing the thickness of an X-ray transmissive member. The phase advance portions 131 and the phase lag portions 132 may be formed such that the phase of the X-rays transmitted through the phase advance portions 131 is different from the phase of the X-rays transmitted through the phase lag portions 132. For example, the phase of the X-rays transmitted through the phase advance portions 131 is advanced by it relative to the phase of the X-rays transmitted through the phase lag portions 132. The amount of change in thickness is determined by the wavelength of the X-rays to be used, and the member.

The phase grating 130 typically modulates the phase of the X-rays transmitted through the phase advance portions 131 by $\pi$ or $\pi/2$ relative to the phase of the X-rays transmitted through the phase lag portions 132. The former grating may be called $\pi$ phase grating, and the later grating may be called $\pi/2$ phase grating. The modulation amount of a phase is only required to be periodic. For example, modulation may be $\pi/3$ modulation.

Figure 2A:
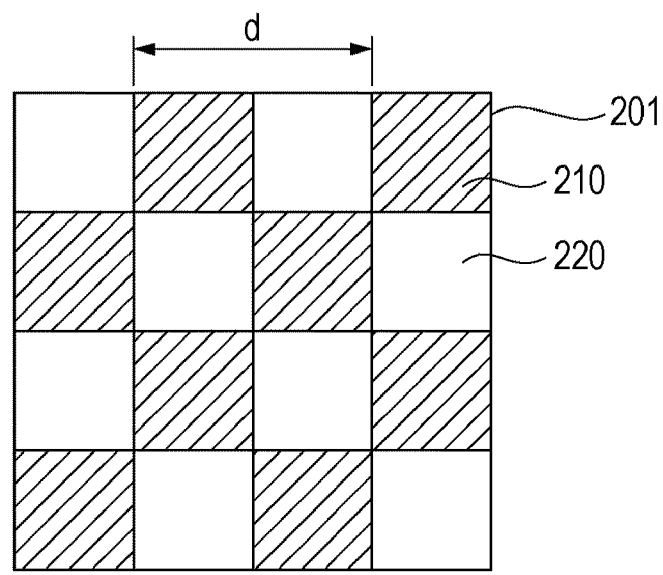
FIGS. 2A and 2B are explanatory views of two-dimensional phase gratings according to second and third embodiments of the present invention.
Figure 2B:
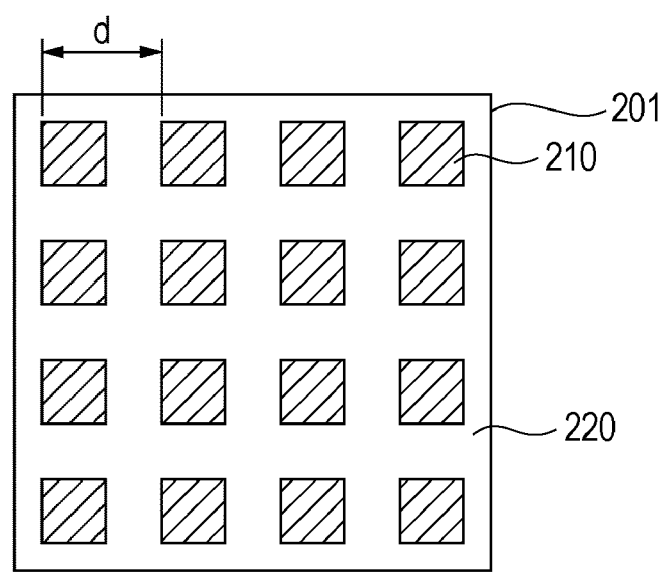

The phase grating 130 may have a one-dimensional linear shape. Alternatively, the phase grating 130 may have a two-dimensional checker board designed pattern as shown in FIG. 2A. Still alternatively, the phase grating 130 may have a lattice-shaped pattern as shown in FIG. 2B. Referring to FIGS. 2A and 2B, reference sign d denotes a period, 201 denotes a two-dimensional phase grating, 210 denotes phase advance portions, and 220 denotes phase lag portions.

The shape of each phase advance portion 210 or each phase lag portion 220 is a square in FIGS. 2A and 2B, however, the outer edge thereof may be deformed into a circular shape through fabrication. Even when the shape is deformed into the circular shape, the deformed portion can be used as a phase grating.

If the phase grating 130 has a one-dimensional period, phase gradient information only in a one-dimensional direction of the subject 120 is acquired. In contrast, if the phase grating 130 has a two-dimensional period, phase gradient information in two-dimensional directions can be acquired, which is advantageous.

The material of the phase grating 130 is desirably a substance that transmits X-rays. For example, the material may be silicon.

An interference intensity distribution formed after the X-rays are transmitted through the phase grating 130 most clearly appears at a position, at which, when $Z_0$ is a distance from the X-ray source to the phase grating 130 and $Z_1$ is a distance from the phase grating 130 to an absorption grating 150, the distance $Z_1$ satisfies the following Expression (1). Herein, the "interference intensity distribution" is a periodic intensity distribution in which the grating period of the phase grating 130 is reflected.

In Expression (1), $\lambda$ is a wavelength of the X-rays and d is a grating period of the phase grating 130.

$$\frac{1}{Z_0} + \frac{1}{Z_1} = \frac{1}{N}\frac{\lambda}{d^2} \tag{1}$$

A value N varies depending on the form of a phase grating, and is a real number that can be expressed as follows. It is noted that a value n is a natural number.

$\pi$ phase grating in one-dimensional array: $N=n/4-1/8$ $\pi/2$ phase grating in one-dimensional array: $N=n-1/2$ $\pi$ phase grating with checker board designed pattern in two-dimensional array: $N=n/4-1/8$ $\pi/2$ phase grating with checker board designed pattern in two dimensions: $N=n/2-1/4$
(Absorption Grating)
The period of the interference intensity distribution is typically smaller than the pixel size of the X-ray detector 170. Hence, the interference intensity distribution cannot be detected in this state. Therefore, the absorption grating 150 is used to generate a Moiré with a period that is larger than the pixel size of the X-ray detector 170, so that the X-ray detector 170 detects the intensity distribution of the Moiré. The absorption grating 150 is desirably provided at a position separated from the phase grating 130 by the distance $Z_1$.

The absorption grating 150 includes transmissive portions 151 and light-shielding portions 152 which are periodically arrayed and arranged to partly shield bright sections of the interference intensity distribution 140 formed by the phase grating 130. Each transmissive portion 151 does not have to have an opening penetrating through the absorption grating 150 as long as the transmissive portion 151 can partly transmit the X-rays. The material of the absorption grating 150 is not particularly limited as long as the material has high absorbency for the X-rays. The material may be, for example, gold.

The period of the absorption grating 150 is equivalent to or slightly different from the period of the interference intensity distribution.

If the absorption grating with a period equivalent to the period of the interference intensity distribution is used, a Moiré is generated by in-plane rotation of the absorption grating. When the period of the interference intensity distribution is represented by D, and the angle defined between the orientation of bright and dark sections in the interference intensity distribution and the orientation of the absorption grating is represented by $\theta$ (here, $\theta \ll 1$), the period Dm of the Moiré is $D/\theta$.

In contrast, if the absorption grating with the period slightly different from the period of the interference intensity distribution is used, a Moiré is generated without in-plane rotation of the absorption grating. When the period of the absorption grating is expressed by Da=D+δ (here, δ<<D), the period Dm of the Moiré is $D^2/\delta$.

In the absorption grating 150, the transmissive portions 151 may be one- or two-dimensionally arrayed.

Figure 3A:
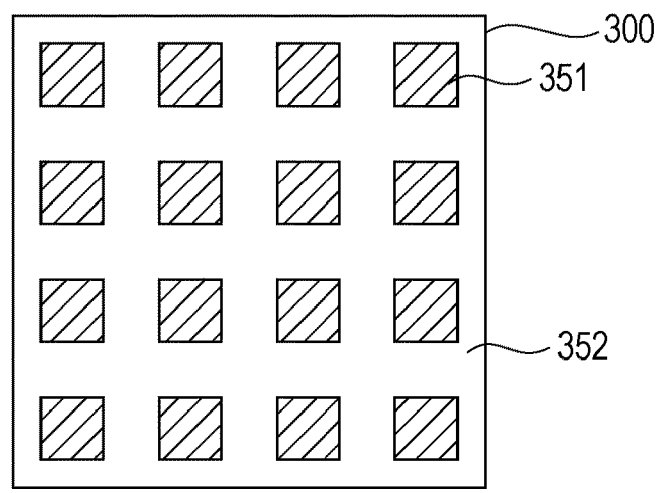
FIGS. 3A and 3B are explanatory views of two-dimensional phase gratings according to the first and second embodiments of the present invention.
Figure 3B:
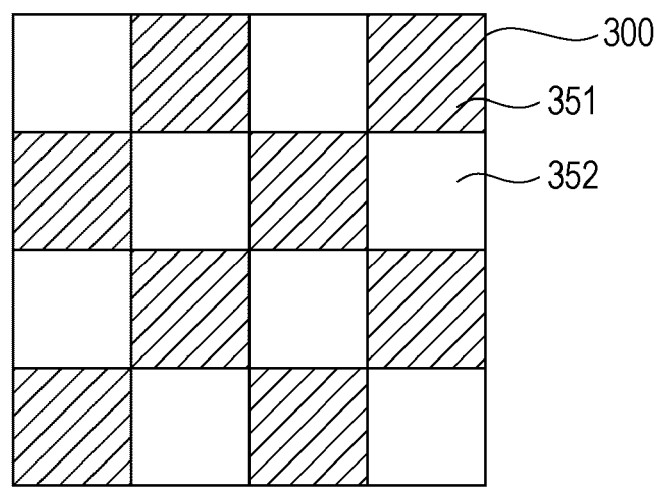

For example, if a π phase grating with a checker board designed pattern shown in FIG. 2A is used, an absorption grating 300 with a lattice-shaped pattern, in which transmissive portions 351 and light-shielding portions 352 are two-dimensionally arrayed as shown in FIG. 3A, is used. If a π/2 phase grating a checker board designed pattern shown in FIG. 2A is used, an absorption grating 300 with a checker board designed pattern, in which transmissive portions 351 and light-shielding portions 352 are two-dimensionally arrayed as shown in FIG. 3B, is used.

The aforementioned combination of the phase grating and the absorption grating is merely an example, and various combinations may be made.

(Detector)

Information of the interference intensity distribution for the X-rays transmitted through the absorption grating 150 is detected as an intensity distribution of the Moiré by the X-ray detector 170. The X-ray detector 170 is an element that can detect the information of the interference intensity distribution for the X-rays. For example, a flat panel detector (FPD) capable of conversion into digital signals may be used.

(Arithmetic Unit)

The information of the intensity distribution of the Moiré detected by the X-ray detector 170 is analyzed by an arithmetic unit 180 through an analysis method, which will be described later, so as to image a differential phase image or a phase image. The acquired differential phase image or phase image is an output image to be displayed on a display unit 190. The arithmetic unit 180 includes, for example, a central processing unit (CPU).

An analysis method for acquiring a phase image from the information of the intensity distribution of the Moiré acquired by the detector will be described below. Then, a processing step executed by the arithmetic unit will be described.

(Analysis Method)

When the interference intensity distribution is formed, many rays of diffracted light are superposed and interfere with each other. Hence, the interference intensity distribution contains a fundamental frequency (hereinafter, referred to as carrier frequency) and a large number of harmonic components of the carrier frequency. A Moiré has a shape in which a carrier frequency component in the interference intensity distribution is spatially spread. When the one-dimensional phase grating with a rule orthogonal to the x axis is used, the Moiré can be expressed by Expression (2).

$$g(x,y)=a(x,y)+b(x,y)\cos(2\pi f_0 x+\phi(x,y)) \quad (2)$$

In contrast, when the two-dimensional phase grating is used, a carrier frequency component in the y direction is superposed on the result of Expression (2).

In Expression (2), the Moiré is expressed by the sum of the background first term and the periodic second term. Herein, a(x, y) indicates the background, and b(x, y) indicates the amplitude of the carrier frequency component. Also, a value $f_0$ indicates the carrier frequency of an interference fringe, and φ(x, y) indicates the phase of the carrier frequency component.

When the π/2 phase grating with the checker board designed pattern is used as the phase grating 130, the carrier frequency component is generated because of interference between zeroth order diffracted light and plus first order diffracted light, and interference between zeroth order diffracted light and minus first order diffracted light. When the π phase grating with the checker board designed pattern is used as the phase grating 130, the carrier frequency component is generated due to interference between plus first order diffracted light and minus first order diffracted light.

For the zeroth order diffracted light and the first order diffracted light, rays separated from one another by a distance Nd are superposed on one another at the phase grating 130. For the plus first order diffracted light and the minus first order diffracted light, rays separated from one another by a distance 2Nd are superposed on one another at the phase grating 130. That is, such interference is shearing interference with a shear amount s corresponding to Nd in the case of the π/2 phase grating, or shearing interference with a shear amount s corresponding to 2Nd.

When the phase image of the subject 120 at the position of the phase grating 130 is W(x, y), a phase φ(x, y) and a phase image W(x, y) have the following relationship.

$$\Phi(x,y)=W(x+s,y)-W(x,y)$$

The value s is typically very small. Thus, the following is obtained.

$$\phi(x, y) \cong s\frac{\partial}{\partial x}W(x, y) \quad (3)$$

Regarding Expression (3), it is found that the phase φ(x, y) is information acquired by differentiating the phase image W(x, y) of the subject 120. Therefore, the phase image W(x, y) of the subject 120 can be acquired by integrating φ(x, y).

Meanwhile, the phase φ(x, y) can be acquired from Expression (2) by Fourier transform. That is, Expression (2) can be expressed as follows.

$$g(x,y)=a(x,y)+c(x,y)\exp(2\pi i f_0 x)+c^*(x,y)\exp(-2\pi i f_0 x) \quad (4)$$

Herein, the following is obtained.

$$c(x,y)=\tfrac{1}{2}b(x,y)\exp[i\phi(x,y)] \quad (5)$$

Therefore, the information of the phase φ(x, y) can be acquired by extracting a component of c(x, y) or a component of c*(x, y) from the interference fringe.

Herein, by the Fourier transform, Expression (4) is as follows.

$$G(f_x,f_y)=A(f_x,f_y)+C(f_x-f_0,f_y)+C^*(f_x+f_0,f_y) \quad (6)$$

Herein, G($f_x$, $f_y$), A($f_x$, $f_y$), and C($f_x$, $f_y$) are two-dimensional Fourier transform for g(x, y), a(x, y), and c(x, y).

Figure 4:
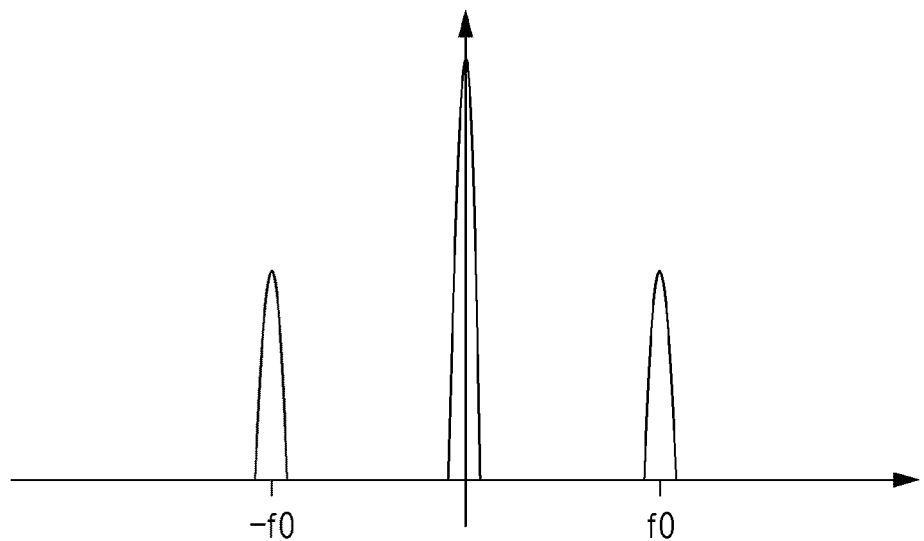
FIG. 4 illustrates a spectrum pattern of an interference intensity distribution.

FIG. 4 is a spectrum pattern of the interference intensity distribution when the one-dimensional grating is used. Typically, three peaks are generated as shown in FIG. 4. The center peak is a peak mainly resulted from A($f_x$, $f_y$). In contrast, peaks on both sides are carrier frequency peaks resulted from C($f_x$, $f_y$) and C*($f_x$, $f_y$). These peaks are generated at positions of ±$f_0$.

Next, a region containing the peak resulted from C($f_x$, $f_y$) or C*($f_x$, $f_y$) is extracted. For example, by extracting the periphery of the peak resulted from A($f_x$, $f_y$) and the periphery of the peak resulted from C($f_x$, $f_y$) or C*($f_x$, $f_y$), the peak resulted from C($f_x$, $f_y$) or C*($f_x$, $f_y$) is separated.

Next, the separated peak resulted from C($f_x$, $f_y$) or C*($f_x$, $f_y$) is moved to an origin in a frequency space, and inverse Fourier transform is performed. By inverse Fourier transform, complex number information is acquired. With the complex number information, the phase φ(x, y), that is, differential phase information is acquired.

Figure 5A:
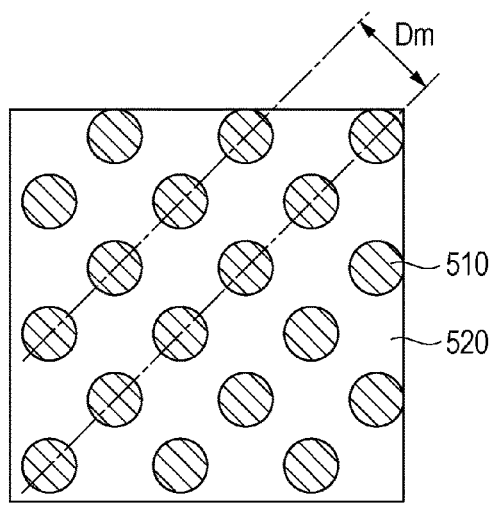
FIGS. 5A to 5D illustrate intensity distributions of Moiré and spectrum patterns when the two-dimensional phase grating is used.

FIG. 5A is an example of an intensity distribution of a Moiré when the π/2 phase grating with the checker board designed pattern (FIG. 2A) and the absorption grating with the lattice-shaped pattern (FIG. 3A) or the absorption grating with the checker board designed pattern (FIG. 3B) are used. Reference sign 510 denotes bright sections of the Moiré, and 520 denotes dark sections of the Moiré. It is to be noted that the intensity distribution of the Moiré is generated in an oblique direction even when the π phase grating with the checker board designed pattern (FIG. 2A) and the absorption grating with the checker board designed pattern (FIG. 3B) are used.

Figure 5B:
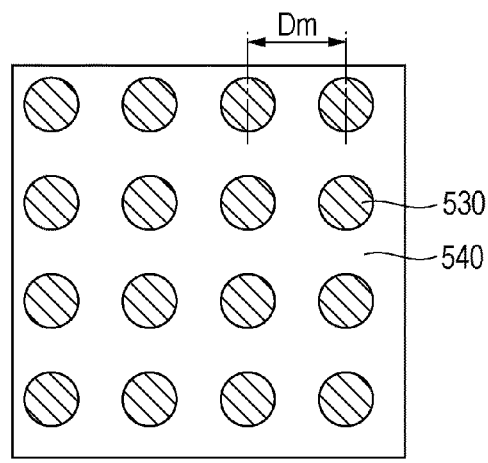

FIG. 5B is an example of an intensity distribution of a Moiré when the π phase grating with the checker board designed pattern (FIG. 2A) and the absorption grating with the lattice-shaped pattern (FIG. 3A) are used. Reference sign 530 denotes bright sections of the Moiré, and 540 denotes dark sections of the Moiré. In this case, the intensity distribution of the Moiré is generated in vertical and horizontal directions.

It is to be noted that the intensity distribution of the Moiré is generated even when the phase grating with the lattice-shaped pattern (FIG. 2B) is used.

Figure 5C:
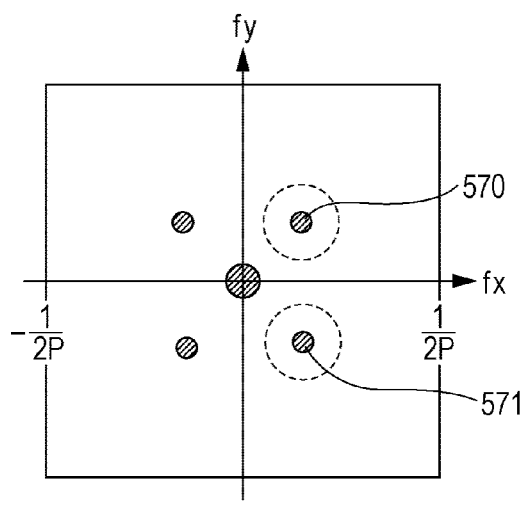
Figure 5D:
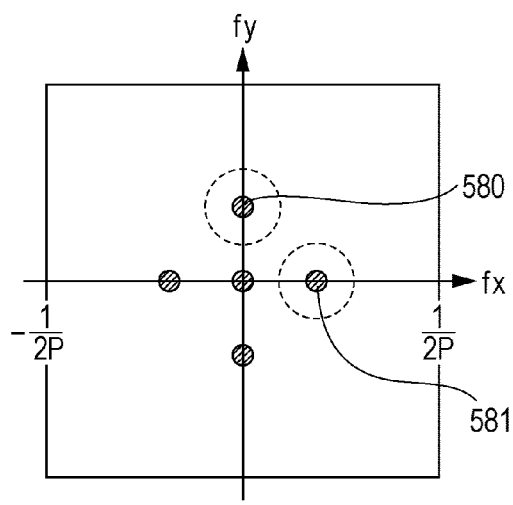

FIGS. 5C and 5D illustrate spatial frequency spectra acquired by performing processing for the intensity distributions of the Moiré shown in FIGS. 5A and 5B by fast Fourier transform (FFT) which is a kind of Fourier transform. The maximum spatial frequency that can be calculated by FFT is 1/(2P) when P is a pixel period of the X-ray detector 170.

The peripheries of two peaks 570 and 571 and peaks 580 and 581, respectively at positions orthogonal to one another, are extracted in a similar manner to the one-dimensional configuration, and are moved to the origin to perform inverse Fourier transform. The extracted regions are indicated by broken lines. By inverse Fourier transform, complex number information is acquired. With the complex number information, differential phase information in the two directions orthogonal to one another is acquired.

Herein, in FIG. 5C, differential phase information in directions at ±45 degrees is acquired. In FIG. 5D, differential phase information in X and Y directions is acquired.

In many cases, the differential phase information thus acquired is folded into (wrapped into) a region of 2π. In particular, when a true phase at any point on a screen is φ(x, y) and a wrapped phase is φ$_{wrap}$(x, y), the following relationship is established.

$$\phi_{wrap}(x,y) = \phi(x,y) + 2\pi n(x,y) \quad (7)$$

where n is an integer which is determined so that φ$_{wrap}$(x, y) is arranged in a region with a width of 2π, for example, a region from 0 to 2π, or a region from −π to +π.

With such information, phase unwrapping is performed for φ$_{wrap}$(x, y) to retrieve the value to the original φ(x, y).

The phase image W(x, y) of the subject can be acquired by integrating φ(x, y) retrieved by Expression (8).

$$W(x, y) = \frac{1}{s} \int \phi(x, y) dx \quad (8)$$

When the one-dimensional grating is used, the integration direction can be only the direction orthogonal to the grating rule direction. Owing to this, to correctly measure the phase image W(x, y), a side of the X-ray detector 170 parallel to the rule direction is irradiated with X-rays that are not transmitted through the subject 120 so that a recognized portion in the phase image W(x, y) is acquired in advance.

When the two-dimensional grating is used, integration can be performed in two directions. The phase image W(x, y) can be correctly measured even if the X-ray detector 170 is entirely irradiated with the X-rays transmitted through the subject 120.

(Processing Step by Arithmetic Unit)

Figure 6:
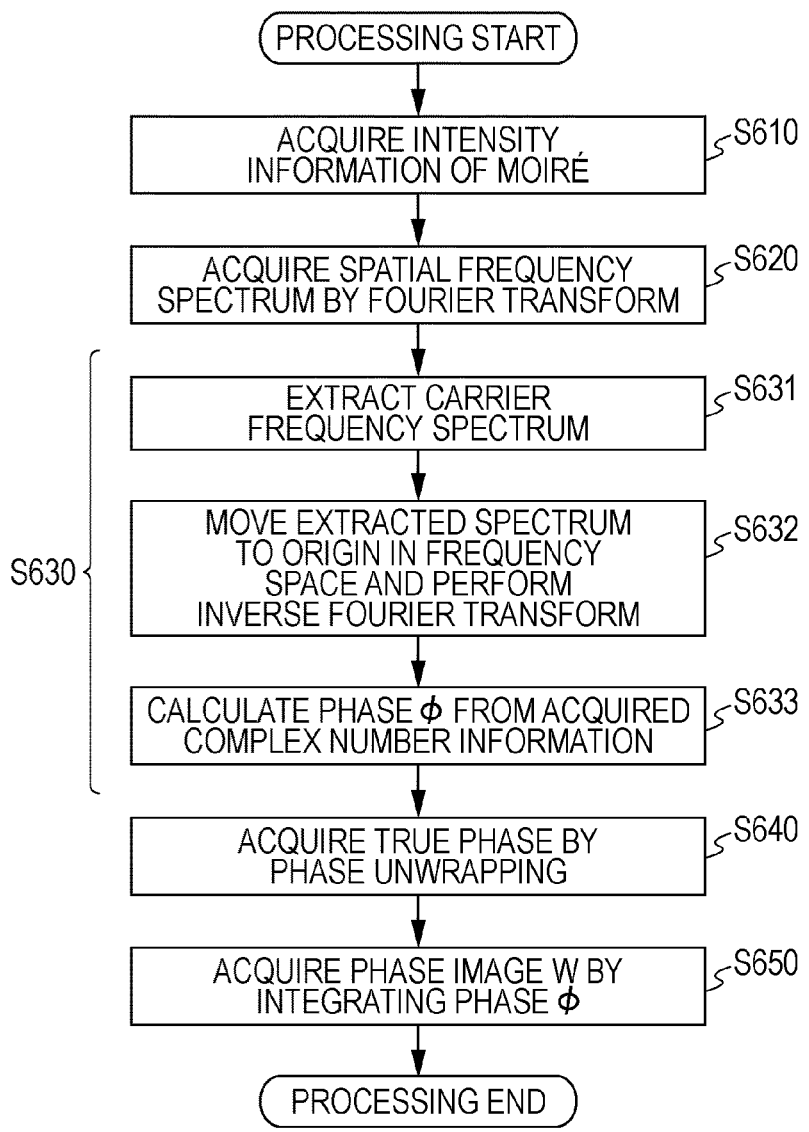
FIG. 6 is an explanatory view of a flowchart of an analyzing method executed by an arithmetic unit according to the present invention.

With regard to the above description, an example of a processing flow executed by the arithmetic unit 180 will be illustrated in FIG. 6.

First, the information of the intensity distribution of the Moiré is acquired from the X-ray detector 170 (S610).

Next, a Fourier transform step is performed (S620) such that Fourier transform is performed for the information of the intensity distribution of the Moiré acquired in S610 and the spatial frequency spectrum is acquired.

Next, a peak separating step is performed (S631) such that the spectrum corresponding to the carrier frequency (spectrum having phase information) is extracted from the frequency space acquired in S620. If it is difficult to extract the spectrum corresponding to the carrier frequency, information of a peripheral region of the spectrum is extracted.

Next, the spectrum extracted in S631 is moved to the origin in the frequency space, and inverse Fourier transform is performed (S632). Accordingly, complex number information having phase information can be acquired.

Next, the phase φ(x, y) as differential phase information is acquired from the complex number information acquired in S632 (S633). It is to be noted that the steps S631, S632, and S633 may be collectively called phase retrieval step (S630).

Next, when φ(x, y) is being wrapped, unwrapping is performed, and the true φ(x, y) is acquired (S640). The step may be called phase unwrapping step. If φ(x, y) is not wrapped, the step S640 may be omitted. Herein, φ(x, y) is differential phase information (differential phase image).

Next, by integrating φ(x, y), the phase image W(x, y) is acquired (S650).

With the above configuration, the X-ray imaging apparatus and the X-ray imaging method that can acquire a phase image of a subject by at least a single imaging operation can be provided. In addition, a program that causes a computer to execute the above steps can be provided.

Second Embodiment

An X-ray imaging apparatus according to a second embodiment of the present invention will be described with reference to FIGS. 7A and 7B. In this embodiment, a spatial resolution is increased rather than the spatial frequency spectrum described in the first embodiment and shown in FIG. 5C.

Figure 7A:
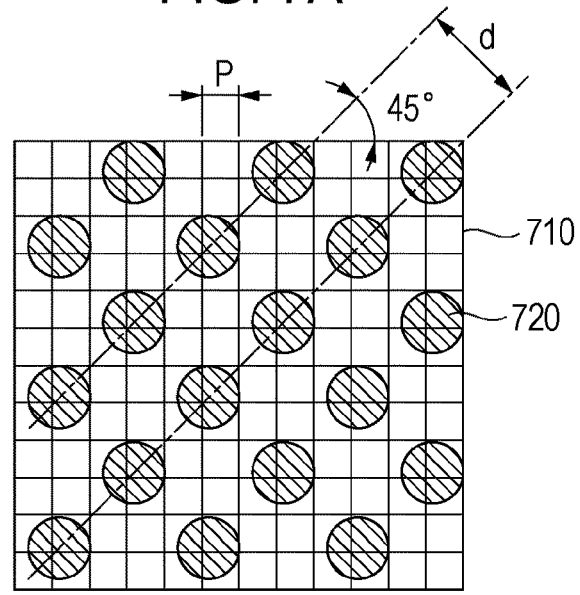
FIGS. 7A and 7B are explanatory views of an intensity distribution of a Moiré and a spatial frequency spectrum according to the second embodiment of the present invention.
Figure 7B:
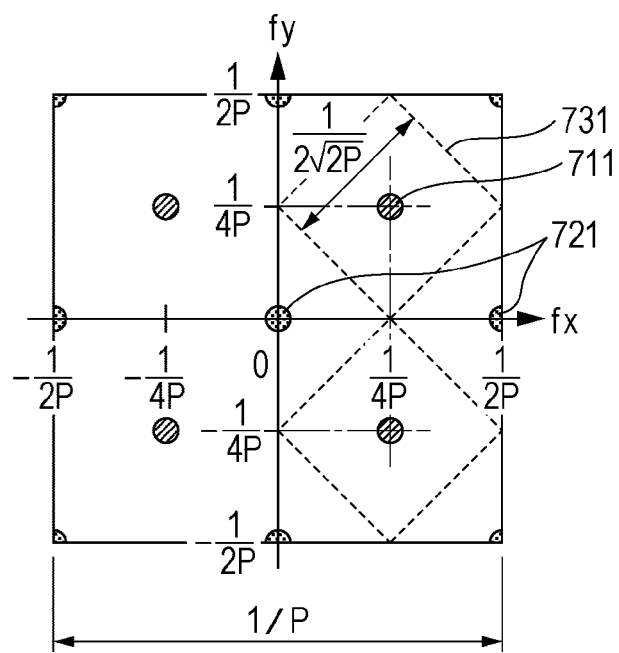

FIG. 7B illustrates a spatial frequency spectrum which is described in this embodiment. To acquire such a frequency spectrum, a fundamental period of a two-dimensional Moiré resulted from an interference intensity distribution and an absorption grating is determined with respect to a pixel period of the X-ray detector to achieve the following ratio.

$2\sqrt{2}$ times

Also, the orientation of the Moiré is adjusted to be inclined at 45 degrees to the pixel array.

FIG. 7A illustrates the intensity distribution of the Moiré on the X-ray detector in this state. Reference sign 710 denotes a light-receiving surface of the X-ray detector, 720 denotes bright sections of the Moiré, d denotes a period of the Moiré, and P denotes a pixel period of the X-ray detector. In this embodiment, the π/2 phase grating with the checker board designed pattern (FIG. 2A) and the absorption grating with the checker board designed pattern (FIG. 3B) are used. However, other phase grating and other absorption grating may be used as long as the intensity distribution of the Moiré to be generated is equivalent.

FIG. 7B is a spatial frequency spectrum acquired by performing FFT for the intensity distribution of the Moiré shown in FIG. 7A. When the number of pixels in the array is n for each of the vertical and horizontal sides, the spectrum space acquired by FFT is discrete data of n×n. The maximum frequency that can be expressed is 1/(2P) when P is a pixel period of the X-ray detector 170.

In this embodiment, the fundamental period of the Moiré is as follows.

$$2\sqrt{2}P$$

Thus, the absolute value of the carrier frequency with that frequency is as follows.

$$1/(2\sqrt{2}P)$$

Also, since the orientation of the Moiré is inclined at 45 degrees, a carrier peak 711 is generated at the following position.

$$\text{Frequency coordinates}(fx,\ fy) = \left(\pm\frac{1}{4P},\ \pm\frac{1}{4P}\right)$$

The carrier peak 711 is a peak corresponding to the carrier frequency of the intensity distribution of the Moiré.

Two adjacent peaks included in four carrier peaks 711 are extracted in the form of a square region inclined at 45 degrees, the square region each having a side expressed as follows.

$$1/(2\sqrt{2}P)$$

After the square region is extracted, the processing described in the first embodiment is performed. Accordingly, the phase image of the subject can be retrieved.

If the spectrum region is extracted by a large area as possible, the spatial resolution can be increased. However, in addition to the peak of the carrier frequency, an unnecessary peak 721 is present in the spectrum space. The unnecessary peak 721 is a peak of a high-frequency component and a DC component and located at a position corresponding to the sum or difference of peak coordinates of carrier frequency components.

If the extraction region is too large, the region around the unnecessary peak 721 may be included. A correct phase image is no longer provided due to the effect of the unnecessary peak 721. Accordingly, the spectrum region to be extracted is an extraction region 731 located at the inner side with respect to the intermediate line between the peak of the carrier frequency and the unnecessary peak 721.

The spatial frequency of the phase image to be retrieved in this embodiment is ½ of the size of the extraction region 731. Thus, as it is found in FIG. 7B, the maximum frequency in the pixel array direction is 1/(4P), and the maximum frequency in the direction at 45 degrees is determined as follows.

$$1/(4\sqrt{2}P)$$

To express the minimum period on a pixel basis, which can be retrieved with the value as the resolution, the minimum period is the reciprocal of the maximum frequency. Thus, the minimum period in the pixel array direction is 4 pixels, and the minimum period in the direction at 45 degrees is as follows:

$$4\sqrt{2}\ \text{pixels} \approx 5.7\ \text{pixels}$$

Comparing with the extraction region in FIG. 5C, the extraction region in FIG. 7B is larger than the extraction region in FIG. 5C, and hence, the spatial frequency that can be retrieved is larger. Thus, with this embodiment, the spatial frequency can be increased as compared with the aforementioned embodiment.

Third Embodiment

An X-ray imaging apparatus according to a third embodiment of the present invention will be described with reference to FIGS. 8A and 8B. In this embodiment, the spatial resolution is increased rather than the spatial frequency spectrum described in the first embodiment and shown in FIG. 5D.

Figure 8A:
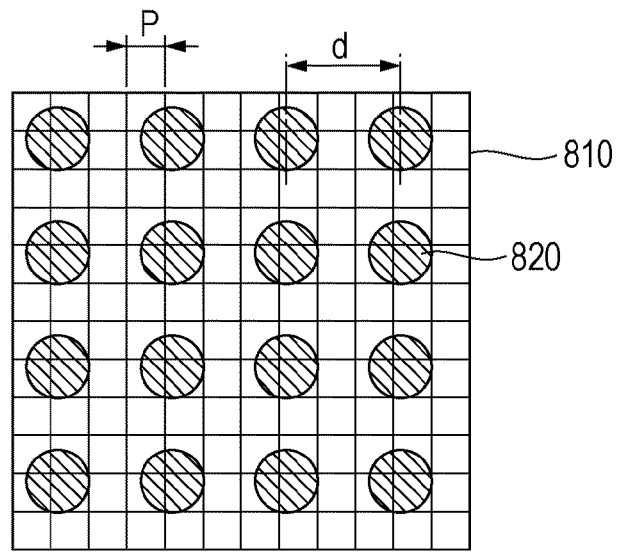
FIGS. 8A and 8B are explanatory views of an intensity distribution of a Moiré and a spatial frequency spectrum according to the third embodiment of the present invention.
Figure 8B:
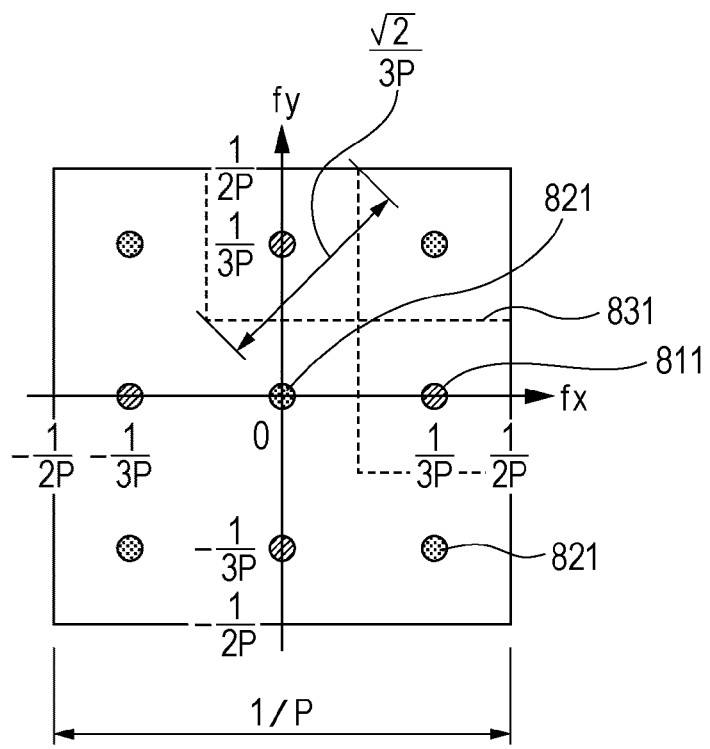

FIG. 8B illustrates a spatial frequency spectrum which is described in this embodiment. To acquire such a frequency spectrum, a fundamental period of a two-dimensional Moiré resulted from an interference intensity distribution and an absorption grating is determined to be three times a pixel period of the X-ray detector, and the orientation of the Moiré is aligned with the pixel array.

FIG. 8A illustrates the intensity distribution of the Moiré on the X-ray detector in this state. Reference sign 810 denotes a light-receiving surface of the X-ray detector, 820 denotes bright sections of the Moiré, d denotes a period of the Moiré, and P denotes a pixel period of the X-ray detector. In this embodiment, the π phase grating with the checker board designed pattern (FIG. 2A) and the absorption grating with the lattice-shaped pattern (FIG. 3A) are used. However, other phase grating and other absorption grating may be used as long as the intensity distribution of the Moiré to be generated is equivalent.

FIG. 8A is a spatial frequency spectrum acquired by performing FFT for the intensity distribution of the Moiré shown in FIG. 8B. Since the fundamental period of the Moiré is 3P in this embodiment, the absolute value of the carrier frequency is 1/(3P). Thus, a carrier peak 811 is generated at the following position.

$$\text{Frequency coordinates}(fx,\ fy) = \left(\pm\frac{1}{3P},\ 0\right) \text{ or } \left(0,\ \pm\frac{1}{3P}\right)$$

The carrier peak 811 is a peak corresponding to the carrier frequency of the intensity distribution of the Moiré. Similar to the second embodiment, erecting square regions each having a side of 1/(3P) are extracted for two adjacent peaks included in four carrier peaks 811. After the square regions are extracted, the processing described in the first embodiment is performed. Accordingly, the phase image of the subject can be retrieved.

However, in this embodiment, in addition to the peak of the carrier frequency, an unnecessary peak 821 is present in the spectrum space. The unnecessary peak 821 is a peak of a high-frequency component and a DC component and located at a position corresponding to the sum or difference of peak coordinates of carrier frequency components. Accordingly, the spectrum region to be extracted is an extraction region 831 located at the inner side with respect to the intermediate line between the peak of the carrier frequency and the unnecessary peak 821.

The spatial frequency of the phase image to be retrieved in this embodiment is ½ of the size of the extraction region 831. Thus, referring to FIG. 8B, the maximum frequency in the pixel array direction is 1/(6P), and the maximum frequency in the direction at 45 degrees is determined as follows.

$$1/(3\sqrt{2}P)$$

To express the minimum period on a pixel basis retrieved with the above value as the resolution, the minimum period is the reciprocal of the maximum frequency. Thus, the minimum period in the pixel array direction is 6 pixels, and the minimum period in the direction at 45 degrees is as follows.

$$3\sqrt{2} \text{ pixels} \approx 4.2 \text{ pixels}$$

Therefore, the spatial resolution in the direction at 45 degrees with respect to the pixel array in this embodiment is better than the second embodiment.

Fourth Embodiment

Figure 9:
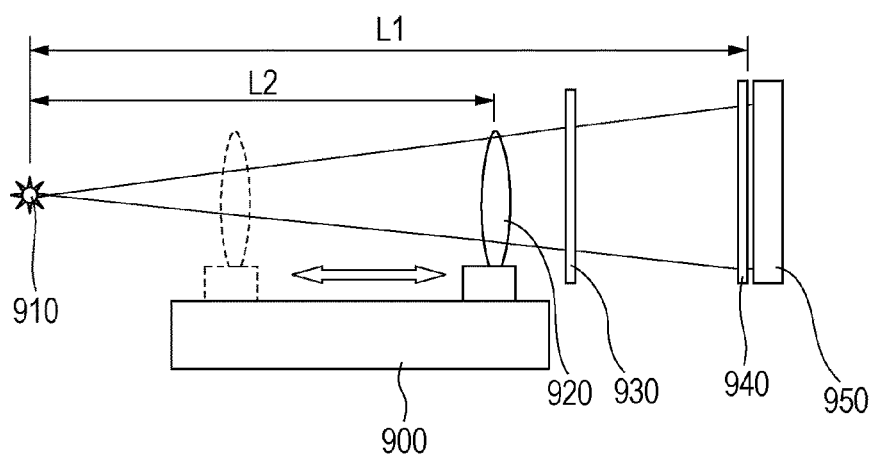
FIG. 9 is an explanatory view of a zoom mechanism according to a fourth embodiment of the present invention.

An X-ray imaging apparatus according to a fourth embodiment of the present invention will be described with reference to FIG. 9. The X-ray imaging apparatus of this embodiment is the X-ray imaging apparatus according to any one of the first to third embodiments including a subject moving device 900. The subject moving device 900 can move a subject 920 along the optical axis of X-rays.

The X-ray detector has a magnification of imaging for the subject 920 of L1/L2 where L1 is a distance from an X-ray source 910 to an absorption grating 940, and L2 is a distance from the X-ray source 910 to the subject 920.

Thus, as the subject 920 is moved closer to a phase grating 930, L2 becomes larger, and imaging can be performed with a low magnification. In contrast, as the subject 920 is moved closer to the X-ray source 910, L2 becomes smaller, and imaging can be performed with a high magnification.

With the present invention, the X-ray imaging apparatus and the X-ray imaging method that can acquire a differential phase image or a phase image of a subject by at least a single imaging operation can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST

110 X-ray source
111 X-ray
120 subject
130 phase grating
150 absorption grating
151 transmissive portion
152 light-shielding portion
170 X-ray detector
180 arithmetic unit

The invention claimed is:

1. An X-ray imaging apparatus for imaging a subject comprising:
   a diffraction grating that forms an interference intensity distribution by diffracting an X-ray from an X-ray source;
   a shielding grating that forms a Moiré by partly shielding the X-ray from the diffraction grating;
   a detector that detects an intensity distribution of the Moiré by detecting the X-ray from the shielding grating; and
   a calculator that obtains information of a differential phase image of the subject by performing Fourier transform on the intensity distribution of the Moiré detected by the detector, wherein the subject is placed between the X-ray source and the diffraction grating, or between the diffraction grating and the shielding grating.

2. The X-ray imaging apparatus according to claim 1, wherein the diffraction grating forms an interference intensity distribution in which bright and dark sections are arranged two-dimensionally,
   wherein the shielding grating forms the Moiré having a two-dimensional period by shielding a part of the X-ray from the diffraction grating, and
   wherein the calculator obtains the information of the differential phase image of the subject in a first direction and in a second direction intersecting with the first direction, by performing Fourier transform on intensity distribution of the Moiré having the two-dimensional period.

3. The X-ray imaging apparatus according to claim 1, wherein the diffraction grating is a phase grating,
   wherein the phase grating has phase advance portions and phase lag portions that are two-dimensionally arranged, and
   wherein the shielding grating has X-ray shielding portions and X-ray transmitting portions that are two-dimensionally arranged.

4. The X-ray imaging apparatus according to claim 2, wherein the first direction and the second direction are orthogonal to each other.

5. The X-ray imaging apparatus according to claim 1, wherein the calculator obtains the phase image of the subject by integrating the information of the differential phase image of the subject.

6. The X-ray imaging apparatus according to claim 1, wherein the calculator is configured to:
   obtain a spatial frequency spectrum by performing the Fourier transform on the intensity distribution of the Moiré,
   extract a spectrum corresponding to a carrier frequency from the spatial frequency spectrum, and
   perform inverse Fourier transform on the extracted spectrum.

7. The X-ray imaging apparatus according to claim 1, wherein the calculator obtains information of at least one of an amplitude or a phase of a carrier frequency component of the Moiré by performing the Fourier transform on the intensity distribution of the Moiré.

8. The X-ray imaging apparatus according to claim 1, wherein the calculator obtains information of an amplitude and a phase of a carrier frequency component of the Moiré using the Fourier transform of the intensity distribution of the Moiré.

9. The X-ray imaging apparatus according to claim 1, wherein the calculator obtains a spatial frequency spectrum of the Moiré by performing the Fourier transform on the intensity distribution of the Moiré.

10. A method of imaging a subject with an imaging apparatus, the method comprising:
   forming an interference intensity distribution by diffracting with a diffraction grating an X-ray from an X-ray source;
   forming a Moiré by partly shielding with a shield grating the X-ray that forms the interference intensity distribution;
   detecting an intensity distribution of the Moiré by detecting the X-ray whose phase is changed by the subject, wherein the subject is placed between the X-ray source and the diffraction grating, or between the diffraction grating and the shielding gratin; and obtaining information of a differential phase image of the subject by performing Fourier transform on intensity distribution of the Moiré.

11. A non-transitory computer-readable medium storing thereon a program that when executed on a computer causes an X-ray imaging apparatus to execute a process to image a subject, comprising:

forming an interference intensity distribution by diffracting with a diffraction grating an X-ray from an X-ray source;

forming a Moiré by partly shielding with a shield grating the X-ray that forms the interference intensity distribution;

detecting an intensity distribution of the Moiré by detecting the X-ray whose phase is changed by the subject, wherein the subject is placed between the X-ray source and the diffraction grating, or between the diffraction grating and the shielding gratin; and obtaining information of a differential phase image of the subject by performing Fourier transform on intensity distribution of the Moiré.

12. An X-ray imaging apparatus comprising:

an X-ray source;

a phase grating that transmits X-rays from the X-ray source and forms an interference intensity distribution by the Talbot effect;

an absorption grating that partly shields the interference intensity distribution formed by the phase grating and generates a Moiré;

a detector that detects an intensity distribution of the Moiré generated by the absorption grating; and an arithmetic unit that images information of a subject from the intensity distribution of the Moiré detected by the detector and outputs the information, wherein the arithmetic unit
performs Fourier transform for the intensity distribution of the Moiréacquired by the detector and acquires a spatial frequency spectrum,
separates a spectrum corresponding to a carrier frequency from the spatial frequency spectrum, and
performs inverse Fourier transform for the separated spectrum and acquires a differential phase image.

13. An X-ray imaging apparatus for imaging a subject comprising:

a diffraction grating that forms an interference intensity distribution by diffracting an X-ray from an X-ray source;

a shielding grating that forms Moiré by partly shielding the X-ray from the diffraction grating;

a detector that detects information of an intensity distribution of the Moiré by detecting the X-ray from the shielding grating; and a calculator that obtains information of a differential phase image of the subject by:
(a) performing Fourier transform on the information of the intensity distribution of the Moiré detected by the detector to acquire a spatial frequency spectrum,
(b) separating a spectrum corresponding to a carrier frequency from the acquired spatial frequency spectrum, and
(c) performing inverse Fourier transform for the separated spectrum, wherein the subject is placed between the X-ray source and the diffraction grating, or between the diffraction grating and the shielding grating.

* * * * *